US006316446B1

(12) United States Patent
Schelberger et al.

(10) Patent No.: US 6,316,446 B1
(45) Date of Patent: Nov. 13, 2001

(54) FUNGICIDAL MIXTURE

(75) Inventors: Klaus Schelberger, Gönnheim; Maria Scherer, Landau; Reinhold Saur, Böhl-Iggelheim; Hubert Sauter, Mannheim; Erich Birner, Altleiningen; Joachim Leyendecker, Ladenburg; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,965

(22) PCT Filed: May 18, 1998

(86) PCT No.: PCT/EP98/02914

§ 371 Date: Nov. 17, 1999

§ 102(e) Date: Nov. 17, 1999

(87) PCT Pub. No.: WO98/53686

PCT Pub. Date: Dec. 3, 1998

(51) Int. Cl.[7] ........................ A61K 31/535; A01N 37/12; A01N 37/18; A01N 37/44

(52) U.S. Cl. ........................ 514/237.5; 514/539; 514/619; 514/622

(58) Field of Search ................................. 514/237.5, 539, 514/619, 622

(56) References Cited

U.S. PATENT DOCUMENTS 4,829,085 * 5/1989 Wenderoth et al. ................ 514/522

FOREIGN PATENT DOCUMENTS

| 120 321 | 10/1984 | (EP) . |
|---|---|---|
| 253 213 | 1/1985 | (EP) . |
| 254 426 | 1/1988 | (EP) . |
| 398 692 | 11/1990 | (EP) . |
| 96/03047 | 2/1996 | (WO) . |
| 97/42821 | 11/1997 | (WO) . |

OTHER PUBLICATIONS

Tomlin, The Pesticide Manual Incorporating The Agrochemical Handbook, 10th Ed. (1995) pp. 351–352.*
Agrow No. 243, Nov. 3, 1995, p. 22.
Azoxystrobin Compositions, Res. Disclosure, Oct. 1996.

* cited by examiner

Primary Examiner—Allen J. Robinson
(74) Attorney, Agent, or Firm—Keil & Weinkauf

(57) ABSTRACT

A fungicidal mixture comprises a) a phenyl benzyl ether derivate of the formula I.a, I.b or I.c,

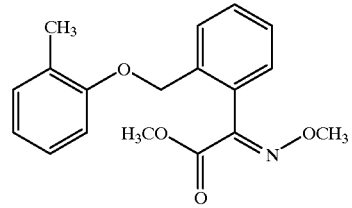

I.a

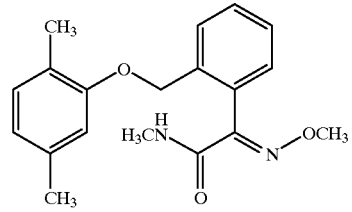

I.b

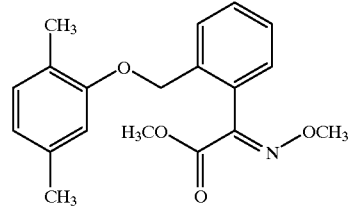

I.c and b) a carboxamide II selected from the group of the compounds IIa and IIb (IIa)

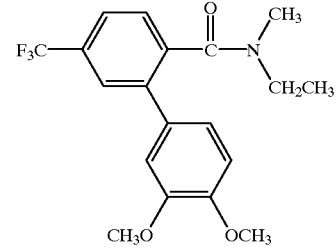

(IIb)

in a synergistically effective amount.

19 Claims, No Drawings

FUNGICIDAL MIXTURE

This application is a 371 of PCT/EP98/02914, filed May 18, 1998.

The present invention relates to a fungicidal mixture which comprises a) a phenyl benzyl ether derivative of the formula I.a, I.b or I.c, I.a
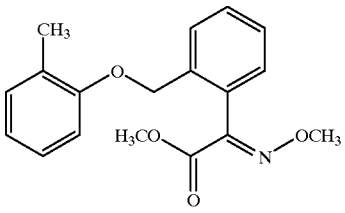

I.b
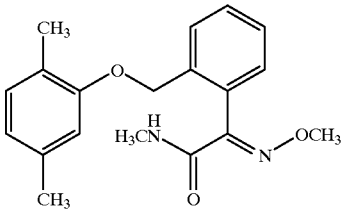

I.c
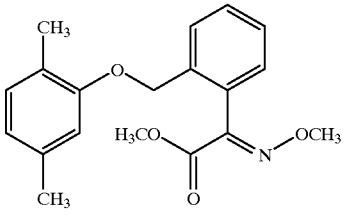

and b) a carboxamide II selected from the group of the compounds IIa and IIb (IIa)
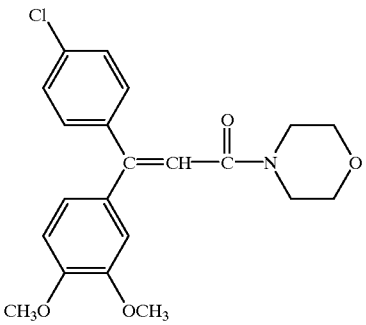

(IIb)
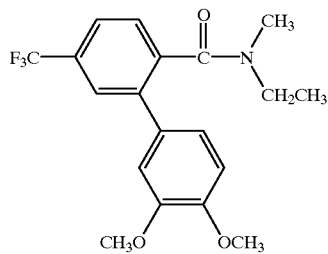

in a synergistically effective amount.

Moreover, the invention relates to methods for controlling harmful fungi using mixtures of the compounds I (I.a, I.b or I.c) and II (II.a or II.b) and to the use of the compound I and of the compound II for the preparation of such mixtures.

The compounds of the formula I, their preparation and their activity against harmful fungi are disclosed in the literature (EP-A 253 213; EP-A 254 426; EP-A 398 692).

Also disclosed are the carboxamides II [IIa: common name: Dimethomorph, EP-A 120 321; IIb: proposed common name: Flumetover, AGROW No. 243 (1995), 22], their preparation and their activity against harmful fungi.

It is an object of the present invention to provide mixtures which have an improved activity against harmful fungi combined with a reduced total amount of active ingredients applied (synergistic mixtures), with a view to reducing the application rates and to improving the activity spectrum of the known compounds.

We have found that this object is achieved by the mixtures defined at the outset. Moreover, we have found that better control of harmful fungi is possible by applying the compound I and the compound II simultaneously together or separately, or by applying the compounds I and the compounds II in succession than when the individual compounds are used.

Owing to their basic character, the compounds I and II are capable of forming salts or adducts with inorganic or organic acids or with metal ions.

Examples of inorganic acids are hydrohalic acids such as hydrofluoric acid, hydrochloric acid, hydrobromic acid and hydroiodic acid, and furthermore sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth sub-group, in particular, chromium, manganese, iron, cobalt, nickel, copper, zinc and others. Particular preference is given to the metal ions of the elements of the sub-groups of the fourth period. The metals can exist in the various valencies which they can assume.

When preparing the mixtures, it is preferred to employ the pure active ingredients I and II, to which further active ingredients against harmful fungi or other pests, such as insects, arachnids or nematodes, or else herbicidal or growth-regulating active ingredients or fertilizers can be mixed, if so required.

The mixtures of the compounds I and II, or the simultaneous joint or separate use of the compounds I and II, exhibit outstanding activity against a wide range of phytopathogenic fungi, in particular from the classes of the Ascomycetes, Basidiomycetes, Phycomycetes and Deuteromycetes. Some of them act systemically and can therefore be employed as folio- and soil-acting fungicides.

They are especially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soya, grapevine, wheat, ornamentals, sugarcane, and a variety of seeds.

They are particularly suitable for controlling the following phytophathogenic fungi: *Erysiphe graminis* (powdery mildew) on cereals, *Erysiphe cichoracearum* and *Sphaerotheca fuliginea* in cucurbits, *Podosphaera leucotricha* in apples, *Uncinula necator* in grapevines, *Puccinia* species in cereals, Rhizoctonia species in cotton, rice and lawns, Ustilago species in cereals and sugarcane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in ground nuts, *Pseudocercosporella herpotrichoides* in wheat and barley, *Pyricularia oryzae* in rice, *Phytophthora infestans* in potatoes and tomatoes, *Plasmopara viticola* in grapevines, Pseudocercosporella species in hops and cucumbers, Alternaria species in vegetables and fruit, Mycosphaerella species in bananas and Fusarium and Verticillium species.

Furthermore, they can be used in the protection of materials (eg. in the protection of wood), for example against *Paecilomyces variotii*.

The compounds I and II can be applied simultaneously, either together or separately, or in succession, the sequence, in the case of separate application, generally not having an effect on the result of the control measures.

The compounds I and II are usually used in a weight ratio of 20:1 to 0.005:1, preferably 10:1 to 0.01:1, in particular 5:1 to 0.2:1.

Depending on the kind of effect desired, the application rates of the mixtures according to the invention are, in particular in agricultural crops, from 0.01 to 8 kg/ha, preferably 0.1 to 5 kg/ha, in particular 0.5 to 3.0 kg/ha.

Application rates of the compounds I are from 0.01 to 0.5 kg/ha, preferably 0.05 to 0.5 kg/ha, in particular 0.05 to 0.3 kg/ha.

Correspondingly, in the case of the compounds II, the application rates are from 0.005 to 1 kg/ha, preferably 0.1 bis 0.5 kg/ha, in particular 0.1 to 0.3 kg/ha.

For seed treatment, the application rates of the mixture are generally from 0.001 to 250 g/kg of seed, preferably 0.01 to 100 g/kg, in particular 0.01 to 50 g/kg.

If phytopathogenic fungi are to be controlled, the separate or joined application of the compounds I and II or of the mixtures of the compounds I and II is affected by spraying or dusting the seeds, the plants or the soils before the sowing of the plants, or before or after plant emergence.

The fungicidal synergistic mixtures according to the invention, or the compounds I and II, can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should guarantee as fine and as uniform as possible a distribution of the mixture according to the invention.

The formulations are prepared in a manner known per se, eg. by adding solvents and/or carriers. It is usual to admix inert additives, such as emulsifiers or dispersants, with the formlations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers or tributylphenyl polyglycol ethers, alkylaryl polyether alcohols, isotridecyl alcohol, fatty alcohol/ethylene oxide condensates, ethoxylated castor oil, polyoxyethylene alkyl ether or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicic acids, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC).

The compounds I or II, or the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE

The synergistic activity of the mixtures according to the invention was demonstrated by the following experiments:

The active ingredients, separately or together, were formulated as a 10% strength emulsion in a mixture of 63% by weight of cyclohexanone and 27% by weight of emulsifier, and diluted with water to the desired concentration.

Use Example 1

Activity Against *Phytophthora Infestans* on Tomatoes

Leaves of potted plants of the cultivar "Große Fleischtomate" were sprayed to runoff point with an aqueous suspension made from a stock solution of 10% of active compound, 63% of cyclohexanone and 27% of emulsifier. The next day, the leaves were infected with an aqueous zoospore suspension of *Phytophthora infestans*. The plants were subsequently placed in a water-vapor-saturated chamber at 16–18° C. After 6 days, the tomato blight on the untreated, but infected control plants had developed to such an extent that the infection could be determined visually in %.

Evaluation was carried out by determining the infected leaf areas in percent. These percentages were converted into efficacies. The efficacy (E) was calculated as follows using Abbot's formula:

$$E=(1-\alpha)\cdot 100/\beta$$

$\alpha$ corresponds to the fungal infection of the treated plants in % and $\beta$ corresponds to the fungal infection of the untreated (control) plants in %

An efficacy of 0 means that the infection level of the treated plants corresponds to that of the untreated control plants; an efficacy of 100 means that the treated plants were not infected.

The expected efficacy of the mixtures of the active ingredients were determined using Colby's formula [R. S. Colby, Weeds 15, 20–22 (1967)] and compared with the observed efficacies.

Colby's formula: $E = x+y-x\cdot y/100$

E expected efficacy, expressed in % of the untreated control, when using the mixture of the active ingredients A and B at the concentrations of a and b x efficacy, expressed in % of the untreated control, when using active ingredient A at a concentration of a y efficacy, expressed in % of the untreated control, when using active ingredient B at a concentration of b The test results are shown in Tables 2 and 3 below.

TABLE 2

| Ex. | Active ingredient | Concentration of active ingredient in the spray liquor in ppm | Efficacy in % of the untreated control |
|---|---|---|---|
| 1 C | Control (untreated) | (100% infection) | 0 |
| 2 C | Ia | 1.25 | 20 |
|  |  | 0.31 | 0 |
|  |  | 0.08 | 0 |
| 3 C | Ib |  |  |
| 4 C | IIa = dimethomorph | 1.25 | 80 |
|  |  | 0.31 | 40 |
|  |  | 0.08 | 40 |
| 5 C | IIb = flumetover | 1.25 | 10 |
|  |  | 0.31 | 0 |
|  |  | 0.08 | 0 |

TABLE 3

| Mixtures according to the invention | Observed efficacy | Calculated efficacy*) |
|---|---|---|
| 1.25 ppm Ia + 1.25 ppm IIa (mixture 1:1) | 95 | 84 |
| 0.31 ppm Ia + 0.31 ppm IIa (mixture 1:1) | 70 | 40 |
| 1.25 ppm Ia + 1.25 ppm IIb (mixture 1:1) | 75 | 28 |
| 0.31 ppm Ia + 0.31 ppm IIb (Mischung 1:1) | 40 | 0 |
| 0.08 ppm Ib + 0.08 ppm IIa) (mixture 1:1) | 90 | 76 |
| 0.08 ppm Ib + 0.08 ppm IIb (mixture 1:1) | 95 | 60 |

*)calculated using Colby's formula

The test results show that the observed efficacy in all mixing ratios is higher than the efficacy which had been calculated beforehand using Colby's formula.

We claim:

1. A fungicidal composition comprising a) a phenyl benzyl ether I selected from the group of compounds I.a, I.b and I.c,

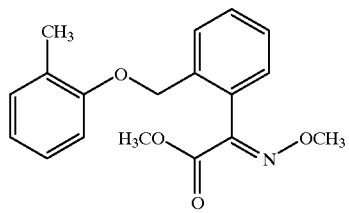

I.a

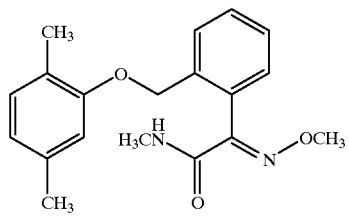

I.b

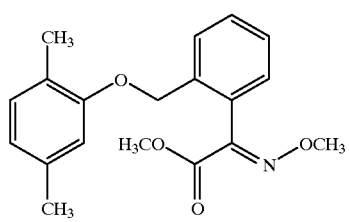

I.c and b) a carboxamide II selected from the group of compounds IIa and IIb

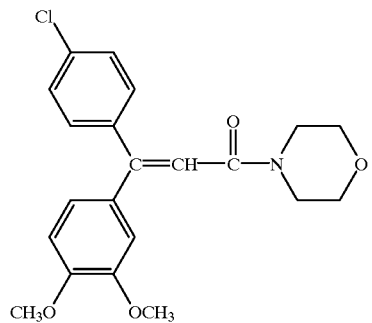

(IIa)

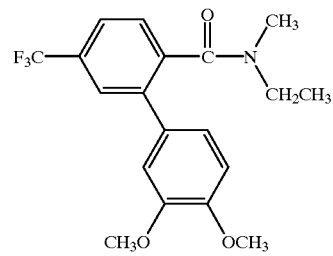

(IIb)

in a synergistically effective amount, and in a weight ratio of the benzyl ether I to the carboxamide II of from 20:1 to 0.005:1.

2. The composition defined in claim 1, wherein the carboxamide II is the compound IIa.

3. The composition defined in claim 1, wherein the carboxamide II is the compound IIb.

4. The composition defined in claim 1, wherein the weight ratio of the benzyl ether I to the carboxamide II is from 10:1 to 0.01:1.

5. The composition defined in claim 1 which is conditioned in two parts, one part comprising the benzyl ether I in a solid or liquid carrier, and the other part comprising the carboxamide II in a solid or liquid carrier.

6. The composition defined in claim 1, wherein the weight ratio of the benzyl ether I to the carboxamide II is from 5:1 to 0.2:1.

7. The composition defined in claim 1, wherein the benzyl ether I is the compound I.a or the compound I.b.

8. A method for controlling harmful fungi, which comprises treating the harmful fungi, their habitat, or plants, seeds, soils, areas, materials or spaces to be kept free from said fungi with an effective amount of the composition defined in claim 1.

9. The method of claim 8, wherein the benzyl ether I and the carboxamide II are applied simultaneously together or separately, or in succession.

10. The method of claim 8, wherein the benzyl ether I is applied in an amount of from 0.01 to 0.5 kg/ha.

11. The method of claim 8, wherein the carboxamide II is applied in an amount of from 0.05 to 1 kg/ha.

12. The method of claim 8, wherein the weight ratio of the benzyl ether I to the carboxamide II is from 10:1 to 0.01:1.

13. The method of claim 8, wherein the weight ratio of the benzyl ether I to the carboxamide II is from 5:1 to 0.2:1.

14. The method of claim 8, wherein the benzyl ether I is applied in an amount of from 0.05 to 0.5 kg/ha.

15. The method of claim 8, wherein the benzyl ether I is applied in an amount of from 0.05 to 0.3 kg/ha.

16. The method of claim 8, wherein the carboxamide II is applied in an amount of from 0.1 to 0.5 kg/ha.

17. The method of claim 8, wherein the carboxamide II is applied in an amount of from 0.1 to 0.3 kg/ha.

18. The method of claim 8, wherein the harmful fungi, their habitat, the plants, the so or the areas are treated with an amount of from 0.01 to 8 kg/ha of the composition.

19. The method of claim 8, wherein the seeds are treated with an amount of from 0.001 to 25 g/kg of the composition.

* * * * *

UNITED STATES PATENT AND TRADEMARK OFFICE
CERTIFICATE OF CORRECTION

PATENT NO. : 6,316,446 B1 Page 1 of 1
DATED : November 13, 2001
INVENTOR(S) : Schelberger et al.

It is certified that error appears in the above-identified patent and that said Letters Patent is hereby corrected as shown below:

Column 8,
Line 2, "0.05" should read -- 0.005 --.
Line 19, "25" should read -- 250 --.

Signed and Sealed this

Thirteenth Day of August, 2002

Attest:

JAMES E. ROGAN
Attesting Officer  Director of the United States Patent and Trademark Office